(12) United States Patent
Jackson et al.

(10) Patent No.: US 12,064,149 B2
(45) Date of Patent: Aug. 20, 2024

(54) RECEIVER FOR MINIMALLY INVASIVE SURGERY

(71) Applicant: Roger P. Jackson, Prairie Village, KS (US)

(72) Inventors: Roger P. Jackson, Prairie Village, KS (US); Lawrence E. Guerra, Mission, KS (US); William R. Hendricks, Overland Park, KS (US)

( * ) Notice: Subject to any disclaimer, the term of this patent is extended or adjusted under 35 U.S.C. 154(b) by 122 days.

(21) Appl. No.: 17/077,613

(22) Filed: Oct. 22, 2020

(65) Prior Publication Data

US 2021/0106365 A1 Apr. 15, 2021

Related U.S. Application Data

(63) Continuation of application No. 16/142,610, filed on Sep. 26, 2018, now abandoned, which is a continuation of application No. 14/833,899, filed on Aug. 24, 2015, now abandoned, which is a continuation of application No. 14/197,848, filed on Mar. 5, 2014, now abandoned.

(60) Provisional application No. 61/852,626, filed on Mar. 15, 2013.

(51) Int. Cl.
A61B 17/70 (2006.01)

(52) U.S. Cl.
CPC ...... *A61B 17/7086* (2013.01); *A61B 17/7085* (2013.01)

(58) Field of Classification Search
CPC .......................... A61B 17/7085; A61B 17/7086
See application file for complete search history.

(56) References Cited

U.S. PATENT DOCUMENTS

| 8,439,922 | B1* | 5/2013 | Arnold | A61B 17/708 606/279 |
| 2006/0106380 | A1* | 5/2006 | Colleran | A61B 5/4504 606/86 A |
| 2007/0219554 | A1* | 9/2007 | Landry | A61B 17/7035 623/17.16 |
| 2008/0077139 | A1* | 3/2008 | Landry | A61B 17/7085 606/103 |
| 2010/0312287 | A1* | 12/2010 | Jackson | A61B 17/8625 606/305 |

(Continued)

*Primary Examiner* — Samuel S Hanna
(74) *Attorney, Agent, or Firm* — Polsinelli PC

(57) ABSTRACT

A bone anchor system for securing a rod to a head of a shank includes a receiver with upright arms defining an open channel. Each upright arm includes a planar top surface between an upper outer surface and an arcuate top inner edge, a horizontally-extending tool engagement groove below the upper outer surface, and an inner concave surface extending downward from the arcuate top inner edge. The tool engagement groove includes a downwardly-facing upper groove surface, an outwardly-facing inner groove surface, and an opposed upwardly-facing lower groove surface extending outwardly to an outer arm surface having a width greater than the width of the upper outer surface. The bone anchor system also includes tooling with a receiver attachment portion having a downwardly-opening recess with an inner convex surface that is closely receivable with the inner concave surface, and an inwardly-directed protrusion that is closely receivable within the horizontally-extending tool engagement groove.

23 Claims, 10 Drawing Sheets

(56) References Cited

U.S. PATENT DOCUMENTS

| | | | |
|---|---|---|---|
| 2012/0253402 A1* | 10/2012 | McLean | A61B 17/7032 606/264 |
| 2013/0046350 A1* | 2/2013 | Jackson | A61B 17/7037 606/305 |
| 2014/0052187 A1* | 2/2014 | McBride | A61B 17/7085 606/264 |

* cited by examiner

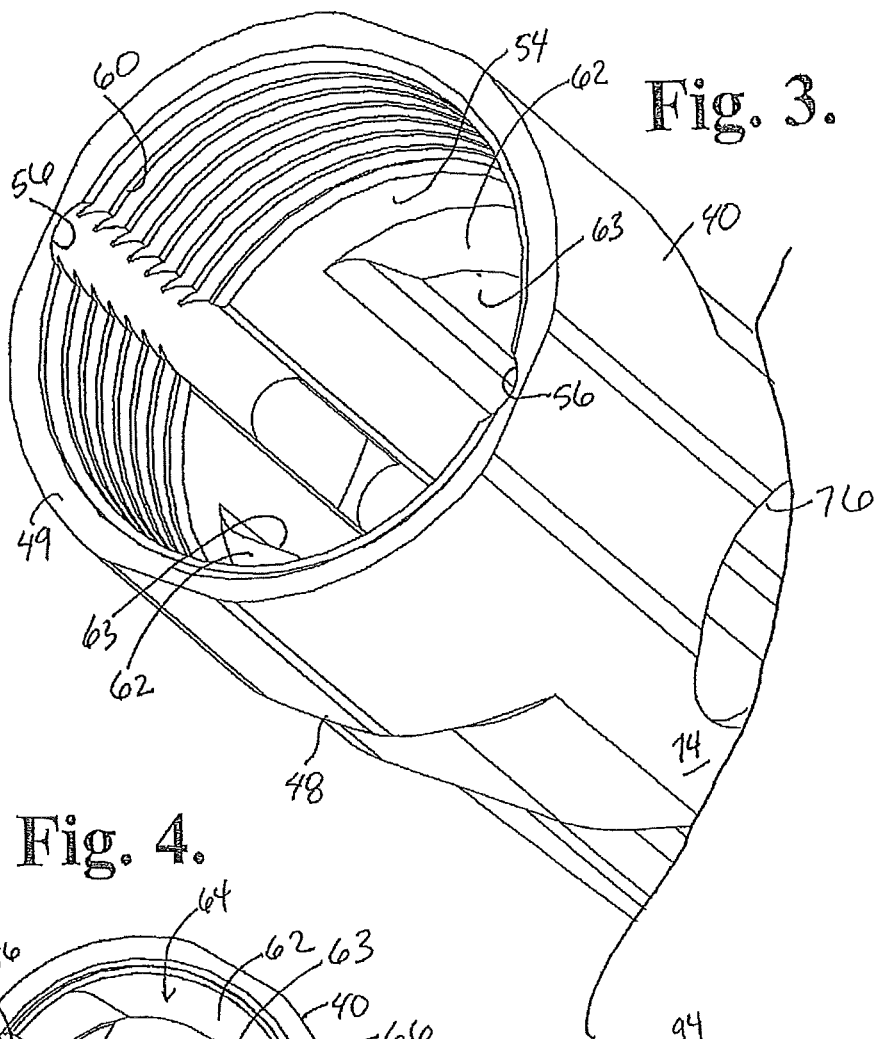
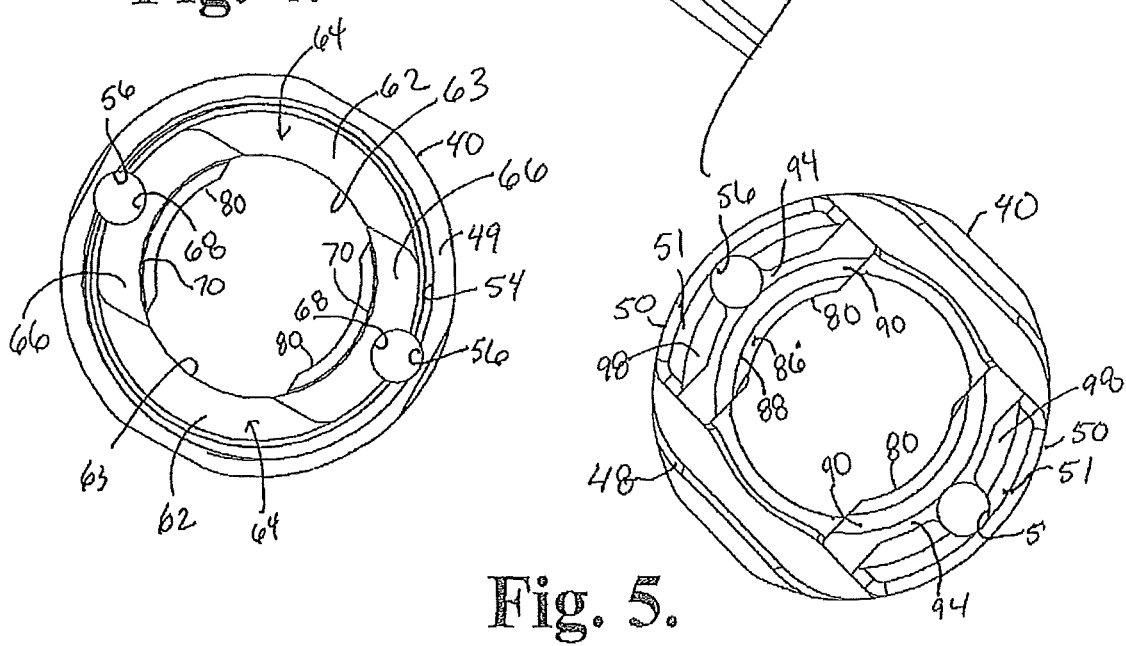

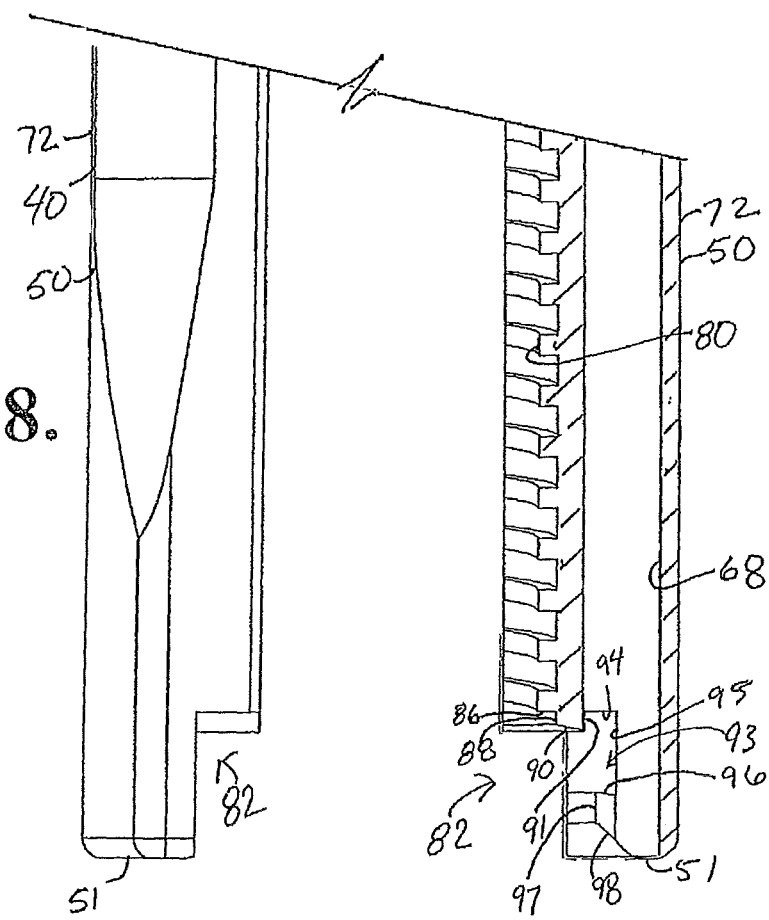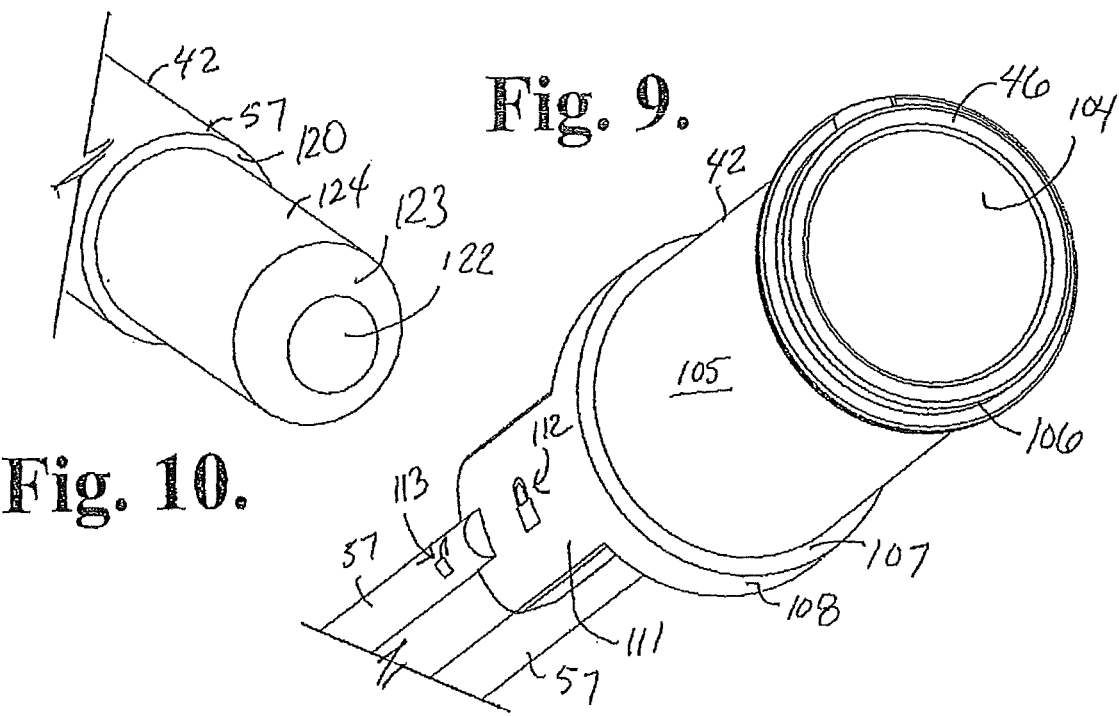

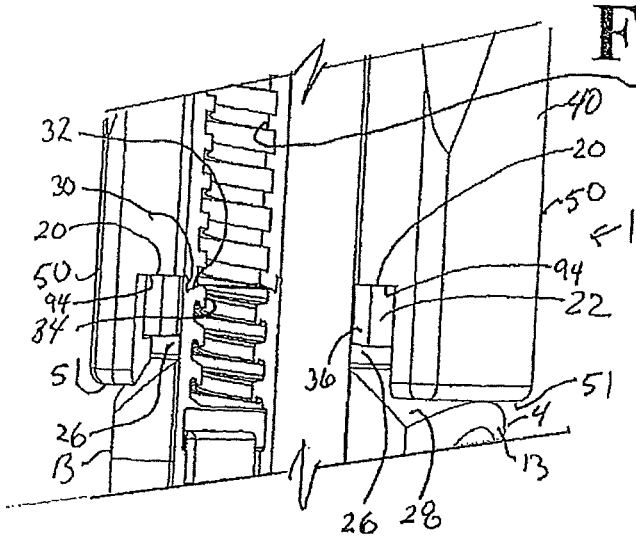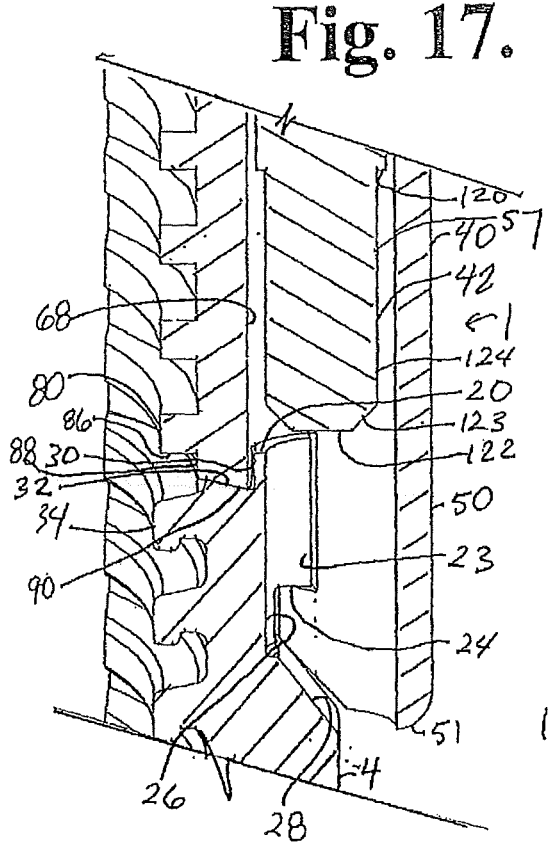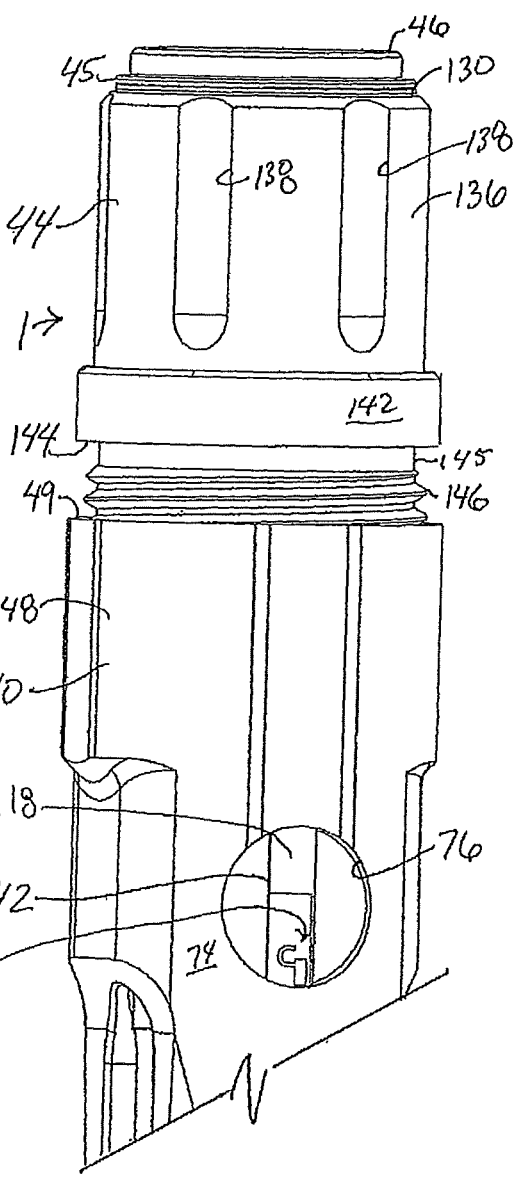

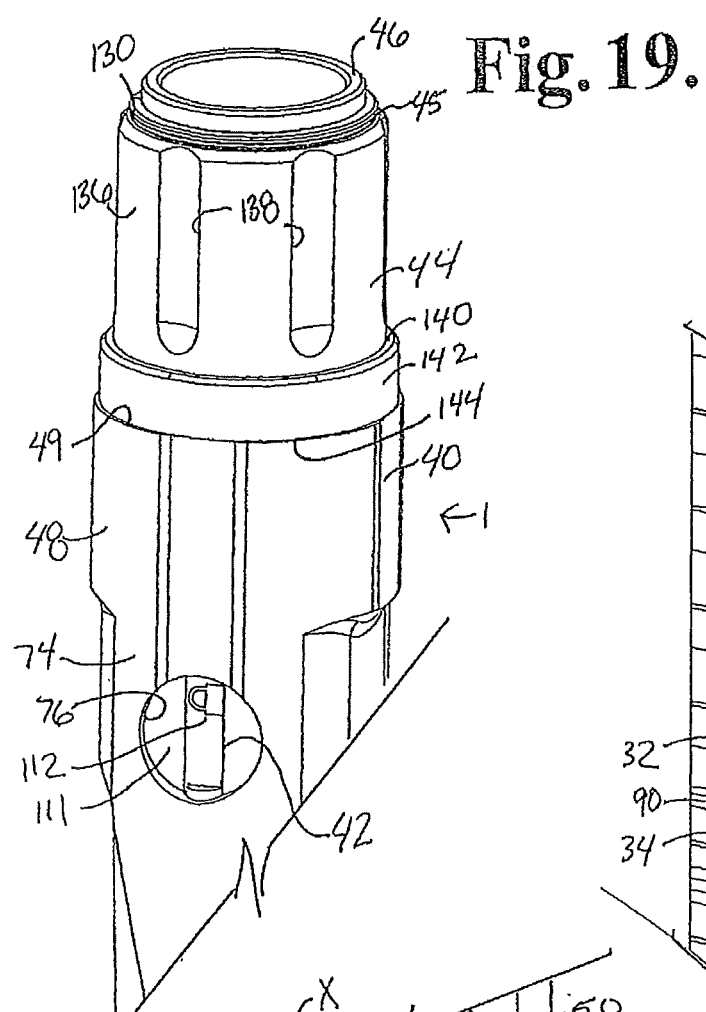
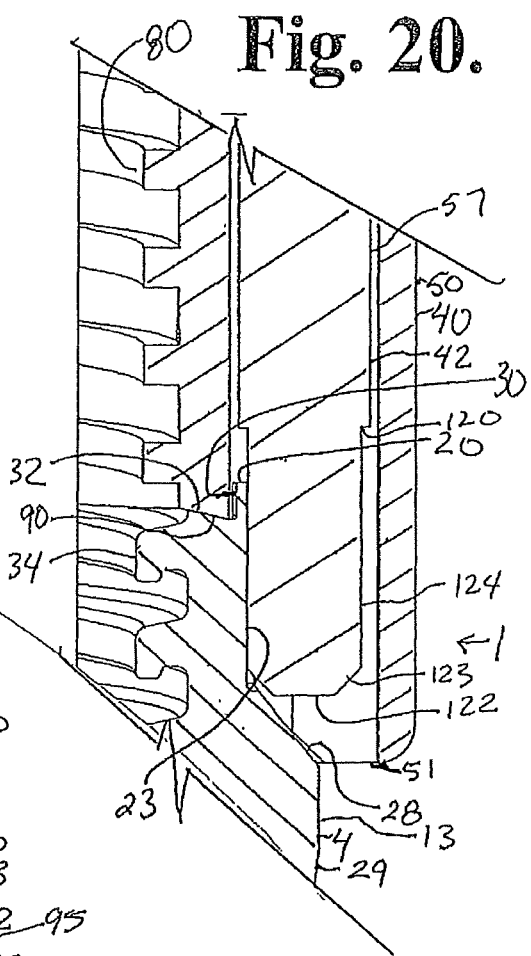
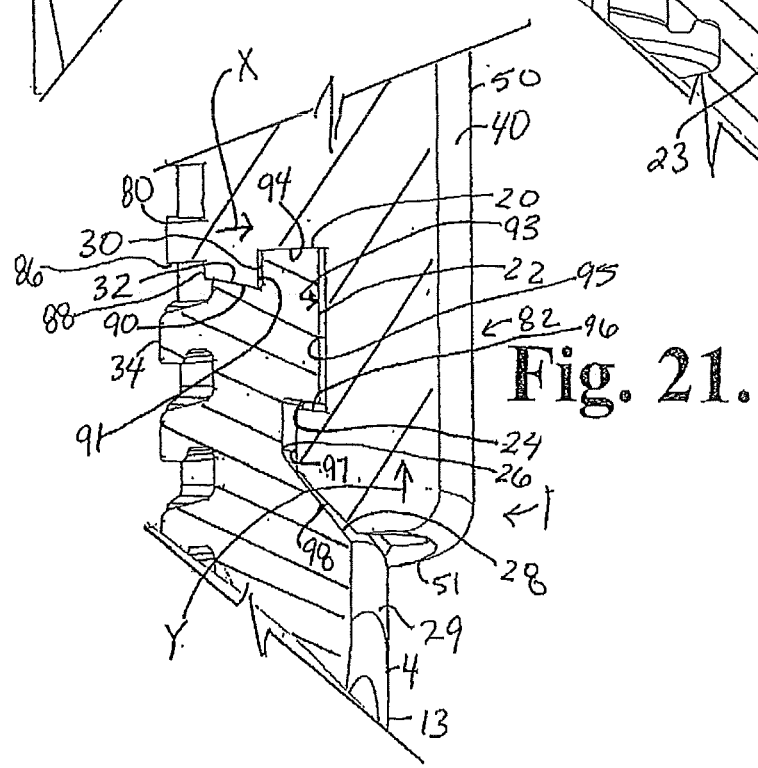

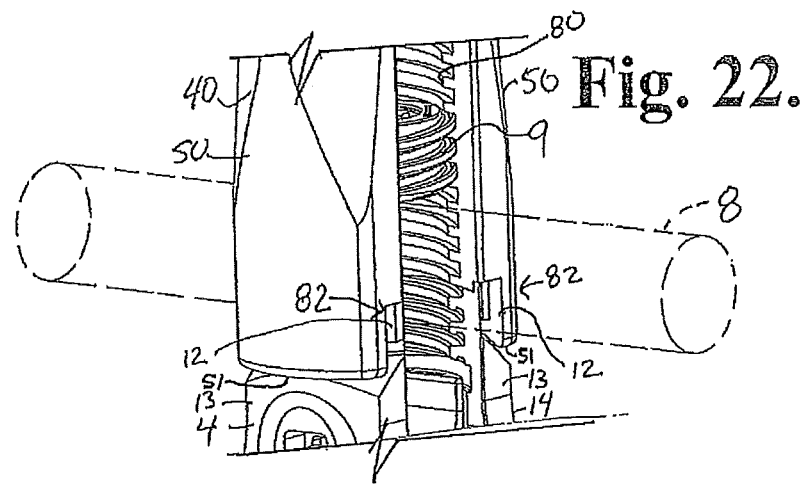
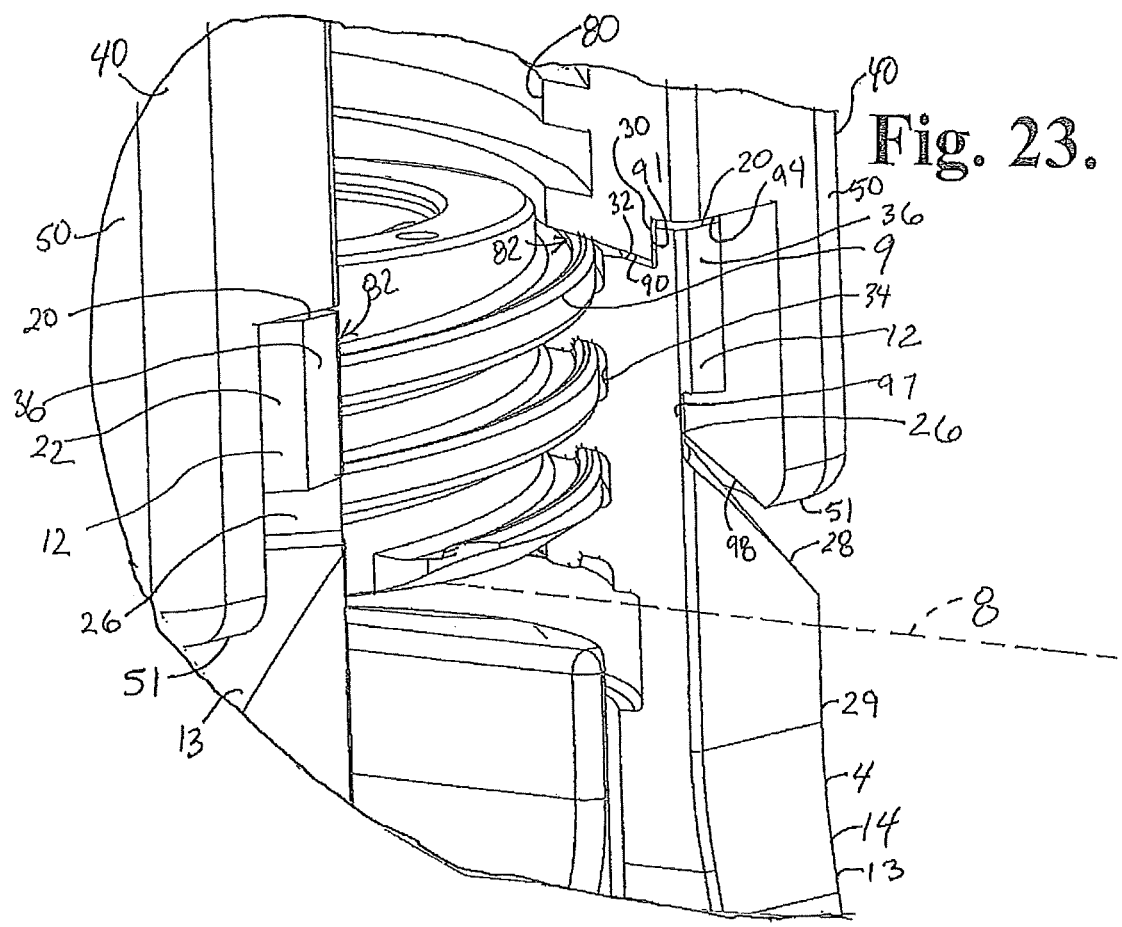

RECEIVER FOR MINIMALLY INVASIVE SURGERY

CROSS REFERENCE TO RELATED APPLICATIONS

This application is a continuation of U.S. application Ser. No. 16/142,610, filed Sep. 26, 2018, which is a continuation of U.S. application Ser. No. 14/833,899, filed Aug. 24, 2015, which is a continuation of U.S. application Ser. No. 14/197,848, filed Mar. 5, 2014, which claims the benefit of U.S. Provisional Application No. 61/852,626, filed Mar. 15, 2013, each of which is incorporated by reference in its entirety herein and for all purposes.

BACKGROUND OF THE INVENTION

The present invention relates to apparatus and methods for use in performing spinal surgery using minimally or less invasive techniques and, in particular, to tools and methods of using such tools, especially for reducing a rod or other longitudinal connecting member into a spinal screw.

For many years, spinal osteosynthesis apparatuses have been utilized to correct spinal deformities, injuries or disease. In such procedures, substantially rigid longitudinal connecting members, for example, elongate solid rods, are surgically attached to vertebrae of the spine to provide support and/or to realign or reposition certain vertebrae. The longitudinal connecting members are typically secured to vertebrae utilizing bone screws and other spinal implants. In order to reduce the impact of such surgery on the patient, a desirable approach is to insert such implants percutaneously or with surgical techniques that are less invasive to the body of the patient.

Problems arise when implant deployment and insertion tools designed for traditional open surgery that is more invasive are utilized in percutaneous or less invasive surgery. The tools may be bulky, oversized or have irregular surfaces or protrusions that can catch and traumatize tissues. A projecting actuator arm or fastening member may be useful with respect to the spinal screw implantation process or the rod reduction process, but there may be insufficient clearance to use such structure and/or such structure may produce additional unwanted trauma which the percutaneous surgery is attempting to avoid. A percutaneous or less invasive procedure also presents challenges in the implantation of elongate connecting members that have historically required a long incision and open wound in order to provide for the length of the connecting member and the space required for the surgeon's hands as well as the tools needed to manipulate the rod. Such problems are then compounded by the implants and insertion tools used with the connecting member.

SUMMARY OF THE INVENTION

A tool assembly according to an embodiment of the invention includes a rotate-on and rotate-off partially tubular and partially open structure providing an open or through channel, the tool for engaging and holding a bone anchor during surgery and particularly during reduction of a rod or other longitudinal connecting member into a receiver or head of a the bone anchor that is typically in the form of a monoaxial or polyaxial bone screw having spaced arms for receiving a rod or other longitudinal connecting member, such screws typically identified as "open" screws. The tool assembly includes structure at a lower end thereof that is operably mateable with outer surfaces of opposed arms of the receiver of the bone anchor. Furthermore the tool structure includes surfaces that engage both inner and outer upper surface portions of each arm of the receiver. Also, the tool structure is sized for rotating on and off of the receiver in either a clockwise or counterclockwise manner, even when a rod is located within the receiver.

A medical implant holding tool according to an embodiment of the invention includes an engagement structure at a lower end thereof operably mateable with opposed arms of an open receiver of a bone anchor, the receiver opposed arms defining a channel for receiving a longitudinal connecting member, an elongate outer holding tool with an upper tubular portion having a top surface and a first helical thread, the tubular portion terminating at a pair of opposed downwardly extending tangs located opposite the top surface, each tang having an aperture and the engagement structure for mating with one of the arms of the bone anchor receiver; and a cap having a bottom surface and a second helical thread sized and shaped for mating engagement with the first helical thread of the outer holding tool, the cap bottom surface engageable with an elongate portion and wherein rotation of the cap with respect to the outer holding tool moves the elongate portion downwardly into a location against an outer surface of the bone anchor, thereby rotationally fixing the holding tool tangs with respect to the bone anchor.

Objects of the invention include providing apparatus and methods that are easy to use and especially adapted for the intended use thereof. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is an enlarged and partial perspective view of a top portion of the outer holding tool.

FIG. 4 is a reduced top plan view of the outer holding tool of FIG. 3.

FIG. 5 is a reduced bottom plan view of the outer holding tool of FIG. 3.

FIG. 8 is a reduced and partial front elevational view of the bottom portion of the tool of FIG. 6 and shown with portions broken away to show the detail thereof.

FIG. 9 is an enlarged and partial perspective view of a top portion of the inner pin support of FIG. 2.

FIG. 10 is an enlarged and partial perspective view of one of the inner pins shown in FIG. 2.

FIG. 16 is a reduced and partial perspective view, similar to FIG. 14 showing the tool assembly in a later stage of assembly with the bone screw.

FIG. 17 is an enlarged and partial front elevational view of the tool assembly and bone screw as shown in FIG. 16 and with portions broken away to show the detail thereof.

FIG. 18 is another partial perspective view of the assembly of FIG. 16 illustrating a top portion of the assembly.

FIG. 19 is a reduced and partial perspective view of the assembly of FIG. 18 shown in a later stage of assembly with the bone screw shown in FIG. 16.

FIG. 20 is an enlarged and partial front elevational view with portions broken away of the assembly of FIG. 19 shown assembled with the bone screw.

FIG. 21 is another partial front elevational view of the assembly of FIG. 20 but showing different portions broken away.

FIG. 22 is a reduced perspective view of the assembly as shown in FIGS. 19 to 21 and further showing a rod and a closure, the rod shown in phantom.

FIG. 23 is an enlarged and partial perspective view of the assembly of FIG. 22 showing the rod reduced into the bone screw and the closure also rotated into the bone screw, the rod shown in phantom.

DETAILED DESCRIPTION OF THE INVENTION

Figure 1:
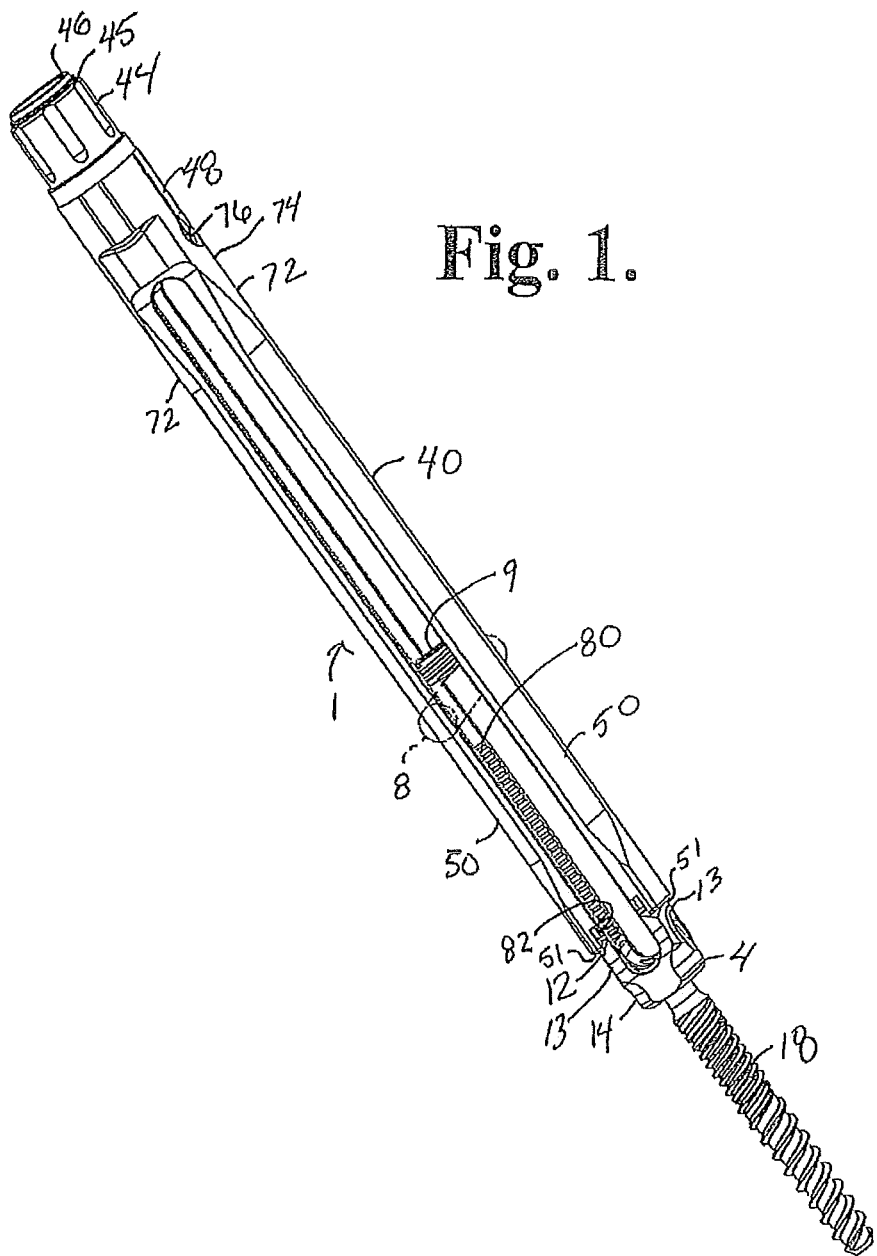
FIG. 1 is a perspective view of a tool assembly according to an embodiment of the invention shown with a polyaxial bone screw, a rod (in phantom) and a closure top.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

It is also noted that any reference to the words top, bottom, up and down, and the like, in this application refers to the alignment shown in the various drawings, as well as the normal connotations applied to such tools and cooperating devices, and is not intended to restrict positioning of the tools in actual use. It is also noted that reference to words such as front, back, anterior and posterior used in this application also refer to the alignment shown in the various drawings, and in particular, when possible, with reference to the human spine and human body, but also is not intended to restrict positioning of the tools in actual use.

With reference to FIGS. 1-23, the reference numeral 1 generally designates a tool assembly according to an embodiment of the present invention that may be used alone or in combination with other tools during various steps of a procedure of inserting two or more bone anchors 4 into vertebrae followed by the installation of a longitudinal member, such as a rod 8 and closure members or tops 9, into the bone screws 4 in a process according to an aspect of the present invention. The tool assembly 1 is particularly configured for reducing the rod 8 down into the bone screw 4 having a dual or two start helical guide and advancement structure thereon that mates with the two or dual-start closure top 9. The multi-start closure top 9 that includes two flange form structures thereon is shown and described, for example, in Applicant's U.S. patent application Ser. No. 13/694,849 filed Jan. 10, 2013, the entire disclosure of which is incorporated by reference herein. The '849 application also discloses other two-start closures, for example two-start reverse angle thread closures and two-start buttress thread closures.

Figure 11:
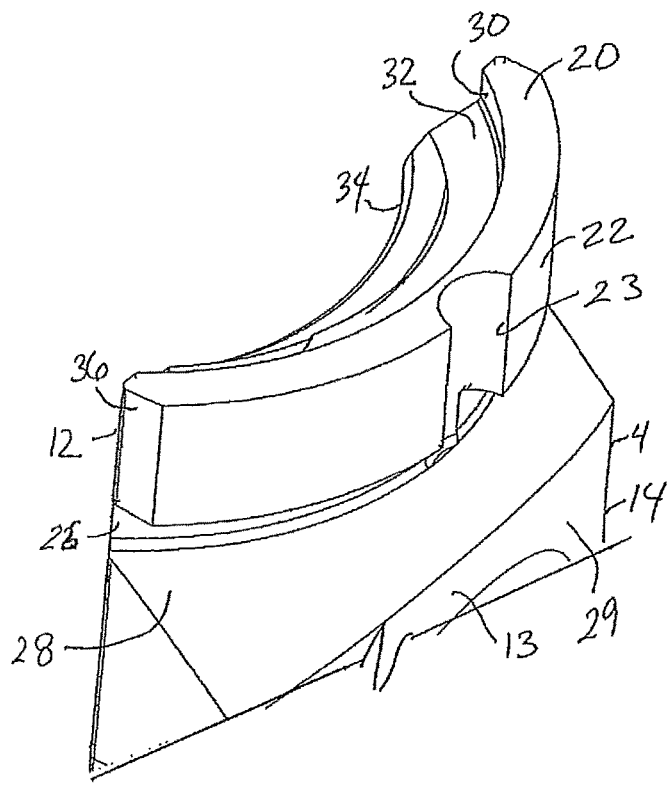
FIG. 11 is an enlarged and partial perspective view of a portion of the bone screw shown in FIG. 1.
Figure 13:
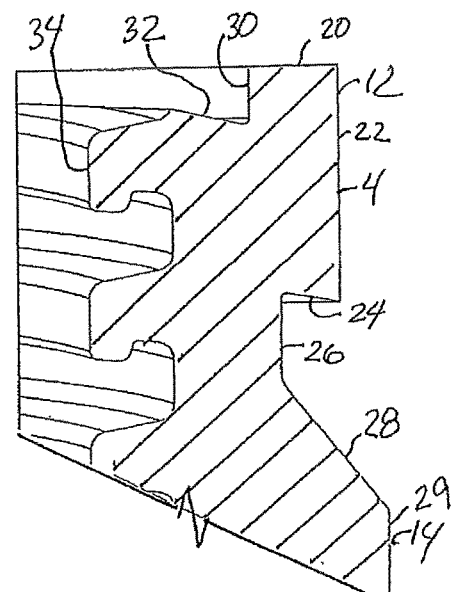
FIG. 13 is an enlarged and partial cross-sectional view taken along the line 13-13 of FIG. 12.
Figure 12:
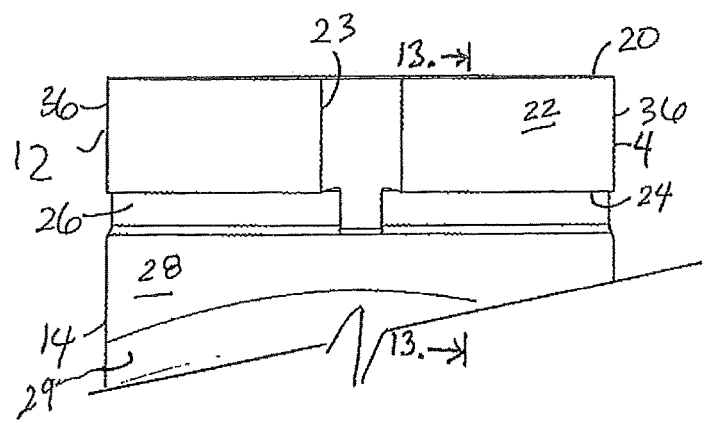
FIG. 12 is a reduced and partial side elevational view of the bone screw portion shown in FIG. 11.

With particular reference to FIGS. 11-13, the tool assembly 1 is designed to cooperate with an upper surface portion 12 located on each opposed arm 13 of a receiver 14 of the bone anchor 4. Although a particular geometry is described herein for the bone anchor upper portion 12, it is noted that tools according to the invention and cooperating bone screw structure may take a variety of forms as long as both inner and outer surface portions of each receiver arm is engaged by the tool assembly. The bone anchor 4 may be polyaxial, mono-axial (one piece, fixed) or other types of hinging or uni-planar pivot screw. The illustrated bone anchor 4 includes a threaded shank 18 that may be articulated (both pivoting and rotation) with respect to the receiver 14 having a base forming an inner cavity with a lower opening and the integral opposed arms 13 extending upward from the base to define the channel for receiving the rod 8, and further includes an inner open retaining ring to capture the head of the shank 18 within the inner cavity of the receiver with the shank extending downward through the lower opening, as well as a lower rod holding compression insert. The inner mechanism for capturing the pivotable shank within the particular bone screw 4 that is partially shown in this application is substantially similar to the assemblies described in detail in U.S. Provisional Patent Application No. 61/795,984 filed Oct. 31, 2012 and incorporated by reference herein (the disclosure of which was incorporated into U.S. Ser. No. 14/061,393 filed Oct. 23, 2013) and therefore will not be described in detail in this application other than to note that the inner open retaining ring can be non-pivotably secured within a lower seating and locking portion of the internal cavity located proximate the lower opening of the receiver. It is also noted that other polyaxial bone screw shanks known in the art may be used in lieu of the particular shank shown in the drawings that is uploaded into the receiver and captured therein by an open retaining ring.

Because the tool assembly 1 may be used with many types of bone anchors, including hooks and other screw types, the illustrations primarily show only the top portion 12 of each arm 13 of the receiver 14 which further includes the following features: a substantially planar top surface 21; an upper outer cylindrical surface portion 22 having a central groove 23; a lower or ledge surface 24 that has an undercut; a lower cylindrical surface portion 26; an outwardly sloping surface portion 28 terminating at an outer surface 29 of the arm 13; an inner cylindrical surface 30 located adjacent the arm top surface 20; an inner sloping surface 32 that extends inwardly to a beginning of a helically would guide and advancement structure 34 that in the illustrated embodiment is a flange form; and opposed substantially planar front and back surfaces 36. As stated above, the top surface 20 is planar and circular or annular. The top surface 20 is located between and adjacent to the outer cylindrical surface 22 and the inner cylindrical surface 30, the surfaces 22 and 30 are both parallel to and run coaxial with a central axis of the receiver 14. The vertical groove 23 formed in the surface 22 is parallel to the receiver axis and is sized and shaped for slidingly receiving one of the support pins of the tool assembly 1 as will be described in greater detail below. The lower undercut surface 24 as best shown in FIG. 13 is adjacent to the cylindrical surface 26 and runs downwardly and outwardly to the cylindrical surface 22, the surface 24 defines an acute angle with the surface 26. The cylindrical surface 26 terminates at the outwardly sloping surface 28 that is illustrated as substantially frusto-conical. The surface 28 terminates at an outer surface 29 of the receiver arm 13 that is illustrated as having a variety of curved and planar surfaces and generally runs downwardly and parallel to the central axis of the receiver. As is shown in FIG. 23, when the rod 8 is captured within the receiver 14, the rod 8 is located below an intersection of the surface 28 and the surface 29.

Figure 2:
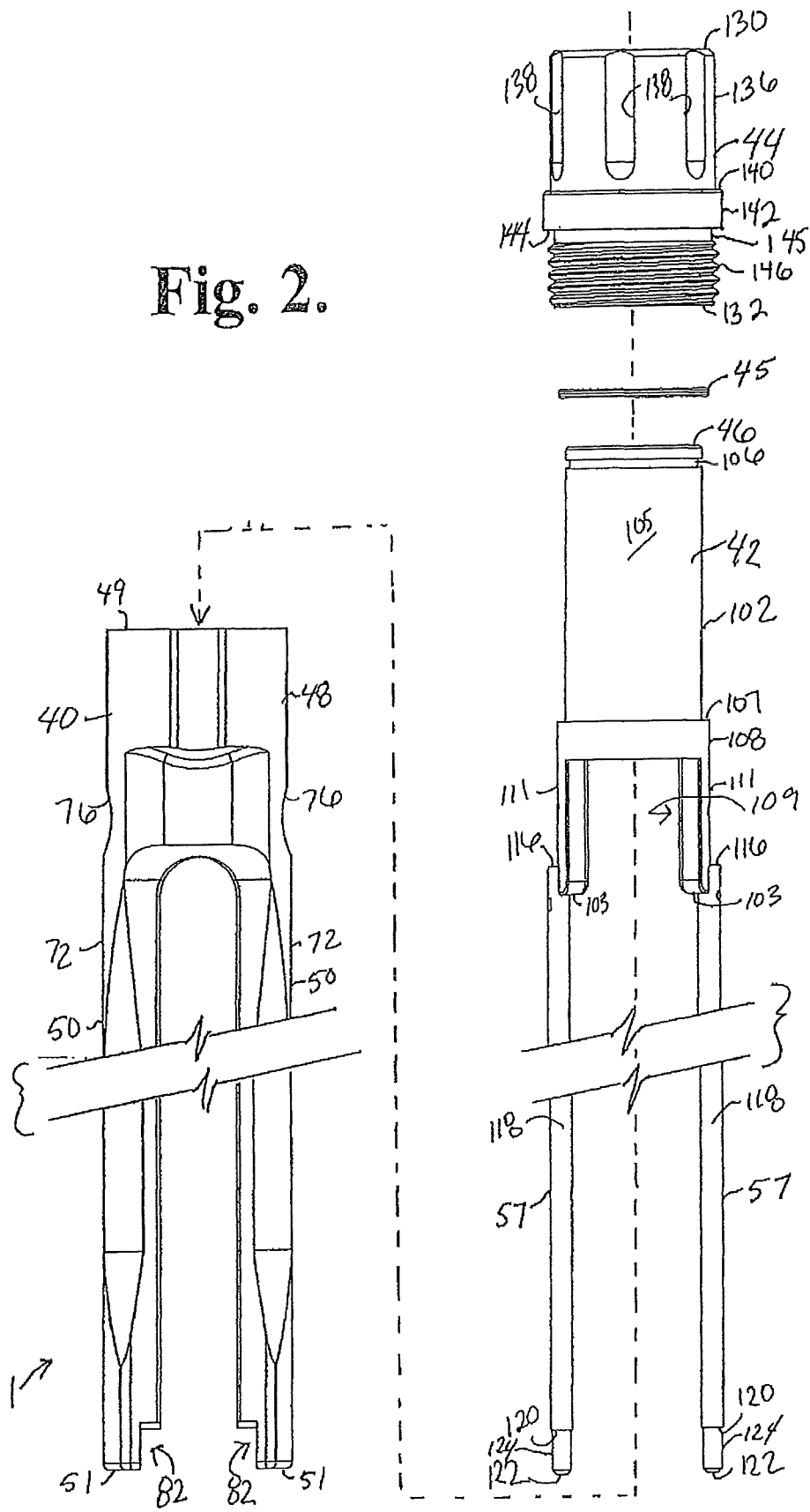
FIG. 2 is a reduced exploded front elevational view of the tool assembly of FIG. 1 including an outer holding tool, an inner pin support, a retaining ring and a threaded cap.

Returning to the tool assembly 1 and particularly to FIGS. 1 and 2, the assembly 1 includes an outer holding tool 40, an inner pin support 42, a threaded cap 44 and associated external deformable and/or elastic retaining or compression ring 45. The holding tool 40 and inner pin support 42 are typically made from harder materials, but a variety of suitable materials are possible, for example, including but not limited to metals, metal alloys, plastics, polymers, composites and blends thereof. For example, the tool components may be made from stainless steel, titanium, polymer blends that may be carbon reinforced, such a polyetheretherketone (PEEK) and or other radiolucent or non-radiolucent materials. In certain embodiments the components 40 and 42 may be rigid and in other embodiments, more flexible, allowing for some flexing or bending without compromising strength of the components. When assembled, the individual components 40, 42, 44 and 45 engage one another as shown in FIG. 1 to result in a holding and guide tool as well as a rod reduction tool that forms a continuous, substantially cylindrical inner pathway from a top surface 46 of the assembled tool 1 (which is the top of the pin support 42) to the engaged bone anchor receiver 24 for receiving tooling and the closure top 9 and or other bone anchor components.

The outer holding tool 40 is elongate and includes an upper tubular and substantially cylindrical portion 48 extending axially from a top surface 49 and generally terminating at an integral pair of opposed downwardly extending prongs, tangs or arms 50, each arm having identical opposed tooling features located near bottom surfaces 51 thereof. The arms or tangs 50 are sized and shaped for forming a through channel from the bottom surfaces 51 to the tubular upper portion 48 for receiving the rod 8 or other longitudinal connecting members or other tools or bone screw components. As best shown in FIG. 1, the tubular portion 48 is relatively short as compared to a length of the opposed tangs or arms 50 that are generally sized and shaped to be sufficiently long to extend from an implanted bone screw 4 through an exterior of a patient's skin so as to provide an outwardly extending and upper handling portion at the tubular portion 48 that allows and provides for gripping by a surgeon during procedures utilizing the tool assembly 1, with or without the other cooperating tools, such as bone screw or closure top drivers to name a few.

Figure 6:
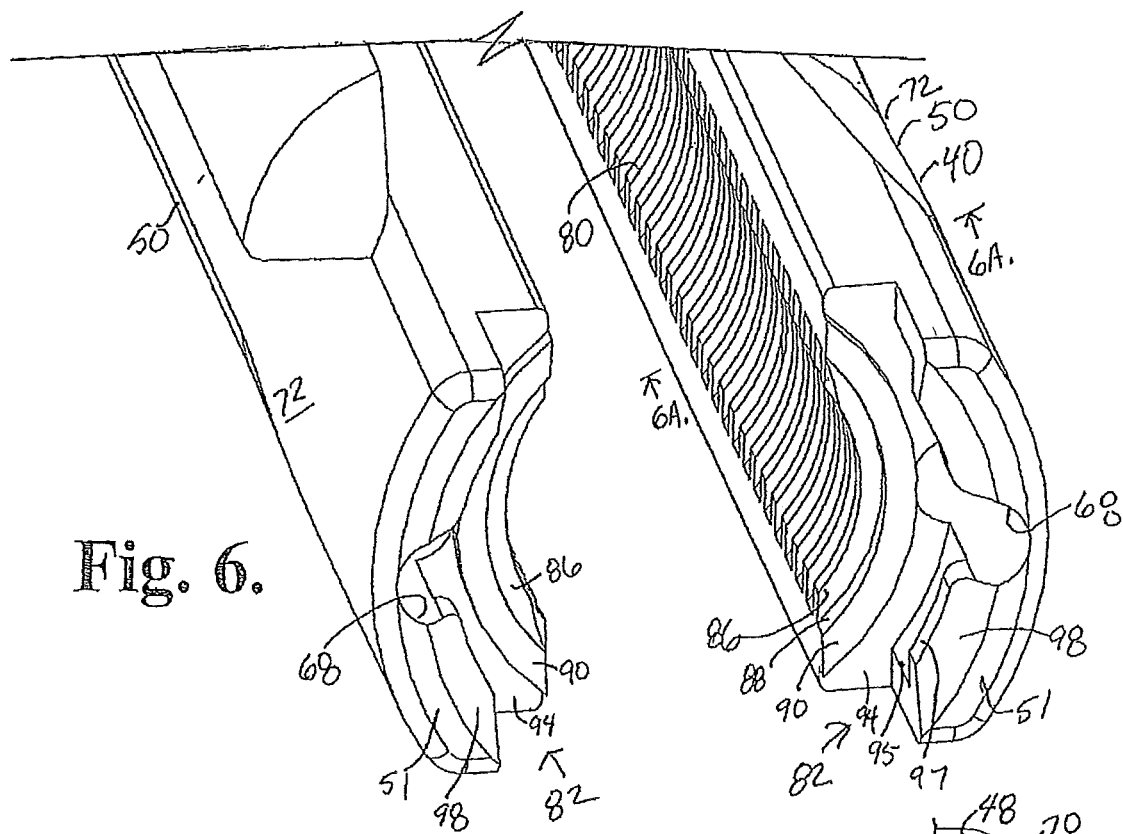
FIG. 6 is an enlarged and partial perspective view of a bottom portion of the outer holding tool.
Figure 6A:
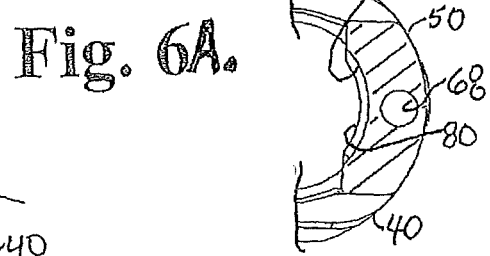
FIG. 6A is a reduced and partial cross-sectional view taken along the line 6A-6A of FIG. 6.
Figure 7:
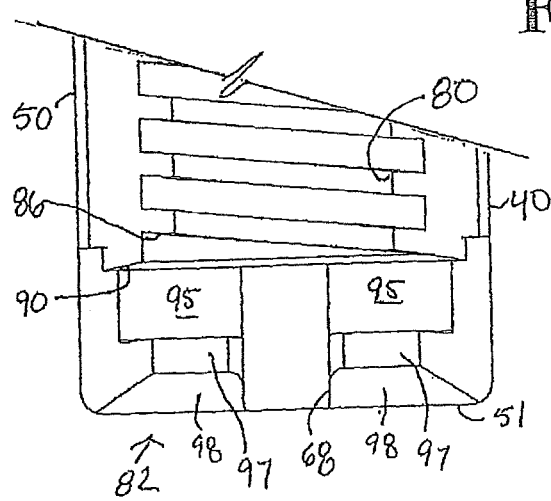
FIG. 7 is a reduced and partial side elevational view of the bottom portion of the tool shown in FIG. 6.
Figures 14, 15:
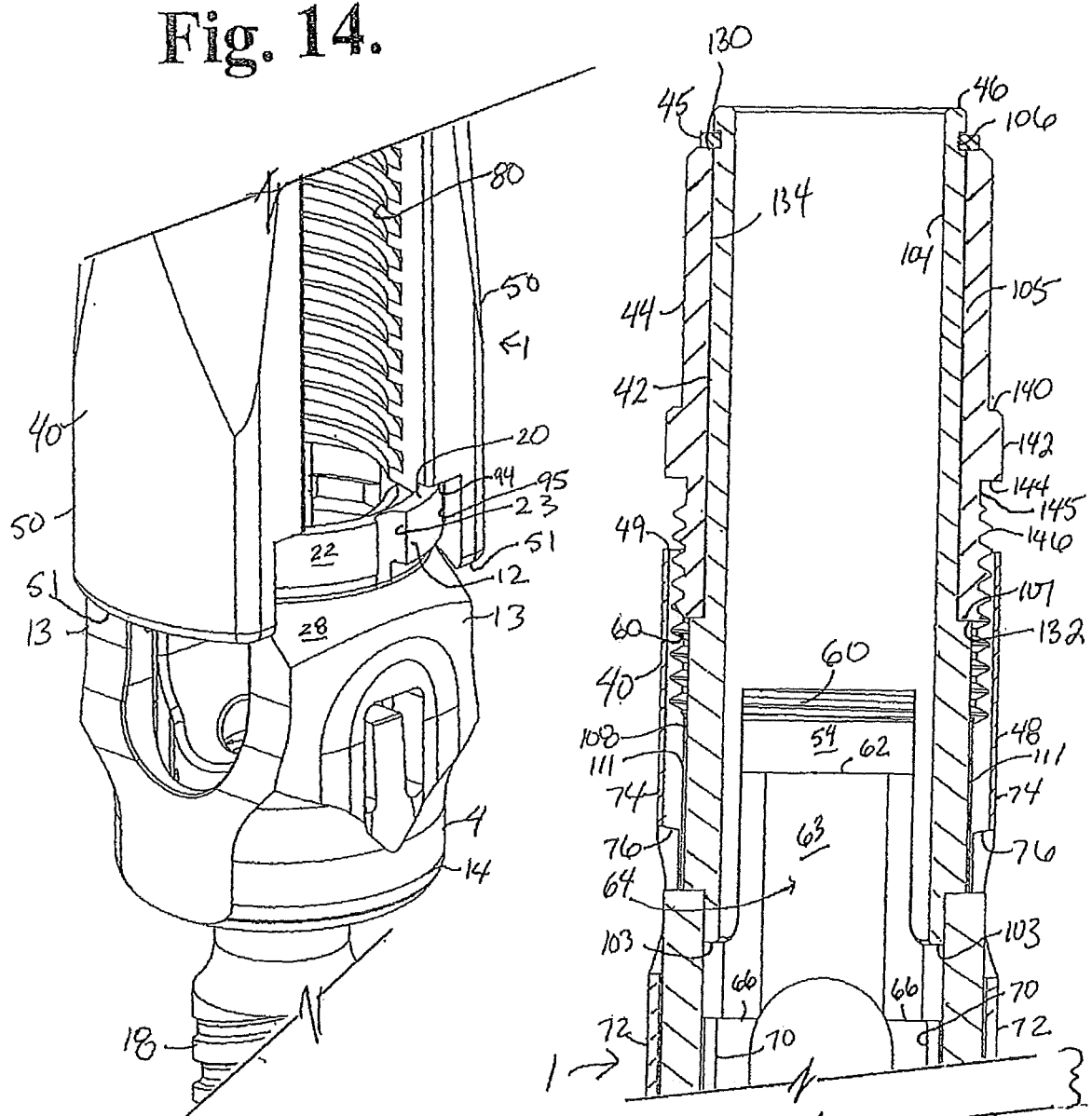
FIG. 14 is an enlarged and partial perspective view of the tool assembly and bone screw shown in FIG. 1, shown in a first stage of assembly.
FIG. 15 is a reduced and partial front elevational view of the tool assembly and bone screw as shown in FIG. 14 and with portions broken away to show the detail thereof.

With particular reference to FIGS. 3, 4 and 15, the outer tool upper tubular portion 48 located at and near the substantially planar and annular top surface 49 further includes an inner substantially cylindrical surface 54 having a pair of opposed grooves 56 sized and shaped for slidingly receiving a pair of spaced cylindrical pins 57 of the inner support 42. The grooves 56 extend axially along an entire length of the tubular portion 48 and are axially aligned with through bores of the arm portions 50 as will be described in greater detail below. Also formed in the surface 54 near the top surface 49 is a helical thread 60 configured for mating under rotation with the threaded cap 44. Located and spaced below the threaded surface 60 is a discontinuous annular seat 62 running perpendicular to and inwardly from the cylindrical surface 54 to an inner cylindrical surface 63. The cylindrical surface 63 has a diameter that is the same as inner surfaces of the tangs 50. The surfaces 62 and 63 partially define a pair of opposed inner tool support features, generally 64, that extend downwardly to the juncture of the upper portion 48 with the elongate tangs 50. A pair of opposed planar surfaces 66 partially define a termination of the tubular structure 48 and the beginning of the spaced tangs 50 that are integral with the tubular upper structure 48. Formed in the surfaces 66 and extending through the otherwise substantially solid arms are through bores 68 aligned with the upper grooves 56 and sized and shaped to closely but slidingly receive the pins 57. For example, see FIG. 6A that illustrates the substantially solid nature of the arms 50 and the cylindrical form of one of the through bores 68. From the surfaces 66 to the bottom 51 of each of the tangs or arms 50, the arms have substantially cylindrical opposed inner surfaces 70 having a diameter the same or substantially similar to the diameter of the inner surfaces 63. The arms further include outer surfaces 72 running along a length of each arm that are also substantially cylindrical and include some other surface contours. Located directly above each arm in a substantially cylindrical outer surface 74 of the upper portion 48 that is contiguous with the arm outer surfaces 72 are a pair of opposed through apertures 76. The apertures 76 provide a window for viewing an indicator printed or stamped on the inner pin support 42 to inform the user whether or not the pins 57 are engaged with the bone screw receiver 14 as will be described in greater detail below.

Moving to a lower portion of each of the arms, at a location approximately two-thirds to three-fourths along a length of the tangs 50, a pair of opposed discontinuous helically wound square threads 80 are formed on each arm inner cylindrical surfaces 70. In the illustrated embodiment, the opposing square thread forms 80 are identical as they are configured for mating with the particular guide and advancement structure 34 of the illustrated bone screw receiver 14 that is a dual or two-start flange form structure. It is noted that the tool inner arms could be equipped with mating flange form structure. However, such is not necessary, as the square thread form 80 is sized and shaped to helically receive the flange forms on the mating closure top 9 and, unlike the flange form structure on the receiver arms, the closure top 9 does not need to frictionally fix upon anything within the tool assembly 1. Therefore, the square thread forms 80 are a more cost effective option. It is noted that the thread forms 80 may be reconfigured for rotatingly receiving and mating with closure tops having different thread-like or non-threadlike helically guide and advancement structures thereon. The assembly 1 advantageously cooperates with dual thread forms, allowing for rotate-on and off of the assembly 1 in either a clockwise or counterclockwise manner as both sides of the cooperating receiver guide and advancement structure are identical for cooperating with the dual-form closure 9. The thread forms 80 terminate at a lower implant engaging portion, generally 82, located near the bottom surfaces 51.

With particular reference to FIGS. 5-8 and 15-17 and FIG. 21, the lowest or bottom of each of the thread forms 80 has a bottom surface 86 that extends radially outwardly to a cylindrical surface portion 88 that is the same as or has a same diameter as the inner cylindrical surface 70 running along the tangs 50 above the square thread forms 80 and up to the tubular upper portion 48. The surface portion 88 terminates at a bottom substantially planar and partially annular surface 90. The surface 90 slopes downwardly and radially outwardly from the cylindrical surface 88 and is sized and oriented to engage and fit closely against the sloping surface 32 of the receiver upper portion 12 that is adjacent the receiver guide and advancement structure 34. Extending upwardly from the tool surface 90 is a cylindrical surface 91 that partially defines a cut-out or recess, generally 93 that is formed into each tang bottom 51 and generally beneath each of the square thread structures 80. As can be seen in FIGS. 8 and 20, for example, each recess 93 extends from the thread form structures 80 generally outwardly toward the arm outer surface 72 a distance that is almost half a diameter of the through bore 68 that receives the pins 57. Additional surfaces that define the recess 93 are a top or ceiling surface 94, an outer concave cylindrical surface 95, a sloped surface 96, a lower cylindrical surface 97 and a lower sloped surface 98 that terminates at or near the tang bottom surface 51. The surface 94 is sized and shaped to closely engage the receiver top surface 20. The outer concave cylindrical surface 95 is sized and shaped to closely engage the outer convex cylindrical surface 22 of the receiver. The sloped surface 96 that slopes downwardly and outwardly toward the surface 95 is sized and shaped to closely receive the sloped surface or undercut 24 of the receiver. The lower concave cylindrical surface 97 is sized and shaped to closely receive the lower convex cylindrical surface 26 of the receiver. Finally, the downwardly and outwardly extending surface 98 is sized and shaped to closely receive the surface 28 of the receiver upper portion 12.

With particular reference to FIGS. 2, 9, 10 and 15, the inner pin support 42 includes an upper tubular portion 102 located near the top surface 46 that is opposite bottom arm end surfaces 103. The upper tubular portion includes an inner cylindrical surface 104 coaxial with an outer cylindrical surface 105. Portions of the inner cylindrical surface 104 extend from the top surface 46 to the arm bottom surfaces 103. An annular recess 106 located near the top surface 46 and formed in the outer surface 105 is sized and shaped for receiving a portion of the retainer ring 45. The outer cylindrical surface 105 extends from the recess 106 to an annular step 107 perpendicular to the surface 105 and extending radially outwardly therefrom. The annular step 107 terminates at an outer cylindrical surface 108, portions of which extend to the bottom arm surfaces 103. Below and near the step 107, a cut-out, generally 109 separates the tubular portion defined by the outer surface 108 and the inner surface 104 into two opposed arms 111 that terminate at respective bottom surfaces 103. Each arm 111 is fixed to one of the elongate pins 57 near top surfaces 116 thereof. Although the illustrated embodiment shows a fixing between the arm 111 outer surfaces 108 and cylindrical surfaces 118 of the pins 57, such as welding, it is noted that each arm 111 may also be integral with the respective adjacent pin 57. Each pin outer surface 118 terminates at a radially inwardly extending ledge 120. A lower pin portion extends downwardly from each ledge and terminates at a bottom surface 122. The lower pin portion is defined in part by a cylindrical surface 124 having a diameter smaller than a diameter of the pin portion 118. A frusto-conical surface 124 that tapers radially inwardly spans between the surface 124 and the bottom 122 that is substantially planar.

The cap 44 as best shown in FIGS. 2 and 15 is tubular and includes an annular top surface 130 and an annular bottom surface 132, the top and bottom surfaces being substantially planar and perpendicular to a central axis of the cap 44. An inner cylindrical surface 134 runs from the top surface 130 to the bottom surface 132. The surface 134 is sized and shaped to slidingly fit over the cylindrical surface 105 of the inner pin support 42. The cap 44 is also sized such that the bottom surface 132 abuts against the surface 107 of the pin support 42 and the top surface 130 abuts against the retainer ring 106. In outer profile, the cap 44 includes a variety of cylindrical surfaces. An upper cylindrical surface 136 located adjacent to the top surface 130 includes a plurality of vertical grooves 138 to aid in handling the tool assembly 1. It is noted that the surface 136 may be smooth or include other grooves, contours, surface treatment to aid in handling of the tool 1. The surface 136 terminates at a radially outwardly extending step 140 perpendicular to the surface 136. The step 140 terminates at another cylindrical surface 142 having a diameter greater than a diameter of the surface 136. The surface 142 terminates at a lower annular ledge surface 144 that is perpendicular to the surface 142 and extends radially inwardly therefrom. The ledge 144 terminates at another cylindrical surface 145 having a diameter smaller than the diameter of the surface 142 and smaller than the diameter of the surface 144. The cylindrical surface 145 is narrow and terminates at a helically wound thread 146 sized and shaped to mate under rotation with the helical inner thread 60 of the outer holding tool 40. For example, with reference to FIGS. 18 and 19, when the pins 57 of the inner pin support 42 are located above the bone screw receiver 14 opposed arms 13 and thus the tool assembly 1 is not fully engaged with the receiver 14, the cap annular surface or lower ledge 144 is spaced from the top surface 49 of the holding tool 40. As can be seen in FIG. 18, at that time, the threaded portion 146 of the cap 44 is not fully mated with the inner threaded portion 60 of the outer holding tool 40. Also, such unlocked position is indicated by the pin surface "unlocked" indicator 113 as viewed through the aperture 76 of the holding tool 40. With reference to FIG. 19, when the pins 57 are engaged and located in the grooves 23 of the receiver arms 13, the cap annular surface or lower ledge 144 abuts against the top surface 49 of the outer holding tool 40. At that time, the "locked" indicator 112 is visible through the aperture 76.

With further reference to FIGS. 2 and 15, the tool components 40, 42, 44 and 45 are typically assembled prior to use and are only dissembled for cleaning purposes. As is indicated by the drawings, the inner pin support 42 pins 57 are slidingly received by the grooves 56 of the upper tubular portion 48 and the through bores 68 of the tangs 50 and the pin support body 42 is slidingly received within the outer holding tool inner cylindrical surface 54. The cap 44 inner cylindrical surface 134 slides over the inner pin support 42 outer surface 105 and the cap is initially rotated with respect to the outer holding tool 40, mating the helical threaded portions 146 and 60 to an extent to bring the pin bottom surfaces 122 to a location generally above the attachment portions 82. With reference to FIG. 15, at this time the outer retaining ring 45 is secured in the annular recess 106 of the inner pin support 42 and against the cap top surface 130.

With reference to FIGS. 14 and 15, the tool assembly 1 is now ready for use with the upper portion 12 of the receiver arms 13. The tool assembly 1 is initially positioned with the tangs 50 lowered to a location between the receiver arms 13 as shown in FIG. 14, the tang surfaces 94 located above the receiver arm surfaces 20. Then the assembly 1 is rotated about the receiver central axis either clockwise or counterclockwise as desired by the user, the surfaces defining the receiver attachment portion 82 of each tang 50 slidingly receiving the upper surfaces of each of the receiver arms 13 as previously described herein with respect to FIGS. 16, 17 and 21. With reference to FIG. 18, at this time, the tangs 50 are not locked into place with respect to the arms as the guide pins 57 are still located above the receiver arm top surfaces 20 as shown in FIG. 17. This unlocked position is indicated by the indicator 113. The cap 44 is then rotated with respect to the outer holding tool 40 until the surface 144 abuts with the surface 49, at which time the pins 57 have been moved into a desired downward position in the receiver grooves 23, blocking any further axial rotation between the tangs 50 and the receiver arms 13. The cylindrical surface 124 is now fully received by the groove surface 23 of each receiver arm 13. The user now sees the "locked" indicator 112 through the tool aperture 76 as shown in FIG. 19. With further reference to FIGS. 22 and 23, as well as to FIG. 21, at this time the dual start closure 9 may be used to reduce the rod 8 down into the receiver 14. As the closure is rotated downwardly, splay of the tool assembly 1 tangs 50 as well as splay of the receiver arms 13 (both outward and inward) is controlled by the tool surfaces 91 pressing outwardly (see arrow X in FIG. 21) against the receiver inner cylindrical surfaces 30 as well as the tool tangs 50 surfaces 96 pulling upwardly (see arrow Y in FIG. 21) and against the undercut surface 24 of each of the receiver arms. The upward force Y stabilizes the tool surface 95 and thus guards against excessive outward splay. The opposing tool surfaces 91 and 95 desirably capture or sandwich the receiver top portion located near the top surface 20.

With reference to FIG. 23, once the closure 9 is fully received within the arms of receiver 14 and fixed against the rod 8 within the receiver, the tool may be removed by rotating the cap 14 relative to the outer tool portion 40 until the pins 57 are lifted away from the receiver top surface 20 as shown in FIGS. 17 and 18. The tool assembly 1 may then be rotated axially either clockwise or counterclockwise back to the position shown in FIG. 14 and then moved upwardly away from the receiver 14. As shown in FIG. 23, the tool assembly 1 is sized such that the tang bottom surfaces 51 are located above the rod 8 top surface, and thus the rod 8 does not impede or prohibit rotation of the assembly 1 in either direction.

It is to be understood that while certain forms of the present invention have been illustrated and described herein, it is not to be limited to the specific forms or arrangement of parts described and shown.

What is claimed and desired to be secured by Letters Patent is as follows:

1. A bone anchor system for securing an elongate rod to a head of a shank via a closure top, the shank including a threaded anchor portion opposite the head configured for implantation into a bone of a patient, the bone anchor system comprising:
    a receiver comprising:
        a pair of integral upright arms extending upward from a base portion to substantially planar top surfaces having arcuate top inner edges centered about a vertical centerline axis of the receiver, the upright arms including opposed internal surfaces extending between a front face and a back face of each upright arm to define an open channel configured to receive the elongate rod, and upper outer surfaces extending downward from the top surfaces opposite the internal surfaces;
        a discontinuous helically wound guide and advancement structure formed into the opposed internal surfaces of the upright arms proximate to the top surfaces and centered about the vertical centerline axis to define at least a portion of a central bore of the receiver;
        an inner concave cylindrical surface extending downward from the arcuate top inner edge of each upright arm toward the discontinuous helically wound guide and advancement structure and parallel with respect to the vertical centerline axis; and
        a horizontally-extending tool engagement groove below the upper outer surface of each upright arm and configured to receive at least one inwardly-directed protrusion of a receiver attachment portion, each of the tool engagement grooves including a downwardly-facing upper groove surface spaced a fixed distance below the top surface of the upright arm, an outwardly-facing inner groove surface extending downwardly from an inner edge of the upper groove surface, and an opposed upwardly-facing lower groove surface extending outwardly from a lower edge of the inner groove surface to an outer arm surface having a diameter or width, as measured across the vertical centerline axis to an outer arm surface on the opposite upright arm, that is greater than a diameter of the upper outer surfaces, with each of the upper groove surface, the lower groove surface, and the inner groove surface extending to the front face and the back face of the upright arm; and
    tooling comprising the receiver attachment portion with a downwardly-opening recess defined in part by an inner convex cylindrical surface, and the at least one inwardly-directed protrusion below the recess with an upward-facing engagement surface, a downward-facing engagement surface, and a bottom surface below the downward-facing engagement surface,
    wherein when the at least one inwardly-directed protrusion of the receiver attachment portion of the tooling is positioned within the tool engagement groove of the receiver, the inner concave cylindrical surface of each upright arm is configured to be closely received by the inner convex cylindrical surface of the recess of the tooling, the lower groove surface of the tool engagement groove is configured to be closely received by the downward-facing engagement surface of the inwardly-directed protrusion, and the bottom surface of the tooling does not extend below a level of a top surface of the elongate rod when the elongate rod is downwardly positioned into the open channel.

2. The bone anchor system of claim 1, wherein the inner concave cylindrical surface extends circumferentially between the front face and the back face of the respective upright arm.

3. The bone anchor system of claim 1, wherein the inner concave cylindrical surface is radially offset from a root surface of the discontinuous helically wound guide and advancement structure.

4. The bone anchor system of claim 1, further comprising an upwardly-facing transition surface extending between the inner concave cylindrical surface and the discontinuous helically wound guide and advancement structure, the inner concave cylindrical surface and upwardly-facing transition surface together defining an upwardly-facing inner tool engagement recess.

5. The bone anchor system of claim 4, wherein the upwardly-facing transition surface of the inner tool engagement recess intersects the discontinuous helically wound guide and advancement structure.

6. The bone anchor system of claim 5, wherein the upwardly-facing transition surface of the inner tool engagement recess is non-perpendicular to the inner concave cylindrical surface across a width thereof between the discontinuous helically wound guide and advancement structure and the inner concave cylindrical surface.

7. The bone anchor system of claim 5, wherein the upwardly-facing transition surface of the inner tool engagement recess slopes downwardly and radially outwardly away from the vertical centerline axis across a width thereof between the discontinuous helically wound guide and advancement structure and the inner concave cylindrical surface.

8. The bone anchor system of claim 1, wherein the inner concave cylindrical surface and the tool engagement groove are configured to provide for rotation of the receiver attachment portion of the tooling above the top surface of the elongate rod in both a clockwise direction and in a counter-clockwise direction.

9. The bone anchor system of claim 1, further comprising a vertical slot formed into the upper outer surface of each upright arm and extending downward from the top surface of the upright arm to at least the upper groove surface of the tool engagement groove.

10. The bone anchor system of claim 9, wherein the inner groove surface of the tool engagement groove is interrupted by the vertical slot.

11. The bone anchor system of claim 9, wherein the vertical slot further comprises an outwardly-facing curvate surface.

12. The bone anchor system of claim 1, further comprising the shank and an open retaining ring positionable within an internal cavity formed into a base portion of the receiver and communicating with a bottom surface of the receiver through a lower opening,
wherein the open retaining ring is configured to capture the head of the shank within the internal cavity of the receiver, with the shank extending downward through the lower opening, prior to securing the elongate rod in a locked configuration with the closure top.

13. The bone anchor system of claim 12 and further comprising the closure top and the elongate rod, wherein the closure top is configured for positioning into the central bore above the elongate rod positioned in the channel and for rotatable engagement with the discontinuous helically wound guide and advancement structure so as to apply a downward force toward the elongate rod to tock the pivotal bone anchor assembly.

14. The bone anchor system of claim 1, wherein the receiver attachment portion of the tooling further comprises a single-piece structure including the inner convex cylindrical surface and the at least one inwardly-directed protrusion with an upward-facing engagement surface.

15. A bone anchor system for securing an elongate rod to a head of a shank via a closure top, the shank including a threaded anchor portion opposite the head configured for implantation into a bone of a patient, the bone anchor system comprising:
a receiver comprising:
a base portion defining an inner cavity with a lower opening and a pair of integral upright arms extending upward from the base portion to substantially planar top surfaces having arcuate top inner edges centered about a vertical centerline axis of the receiver, the upright arms including opposed internal surfaces extending between a front face and a back face of each upright arm to define an open channel configured to receive the elongate rod and upper outer convex cylindrical surfaces extending downward from the top surfaces opposite the internal surfaces, the inner cavity of the base portion configured to receive the head of the shank with the shank extending downward through the lower opening;
a discontinuous helically wound guide and advancement structure formed into the opposed internal surfaces of the upright arms proximate to the top surfaces and centered about the vertical centerline axis to define at least a portion of a central bore of the receiver;
an inwardly-facing inner concave cylindrical surface extending downward from the arcuate top inner edges of each upright arm toward the discontinuous helically wound guide and advancement structure and parallel with respect to the vertical centerline axis; and
a horizontally-extending tool engagement groove below the upper outer convex cylindrical surface of each upright arm, each of the tool engagement grooves including a downwardly-facing upper groove surface spaced a fixed distance below the top surface of the upright arm, an outwardly-facing inner groove surface extending downwardly from an inner edge of the downwardly-facing groove surface, and an opposed upwardly-facing lower groove surface extending outwardly from a lower edge of the inner groove surface to an outer arm surface having a diameter or width, as measured across the vertical centerline axis to an outer arm surface on the opposite upright arm, that is greater than a diameter of the upper outer convex cylindrical surfaces, with each of the upper groove surface, the lower groove surface, and the inner groove surface extending to the front face and the back face of the upright arm; and
tooling comprising a receiver attachment portion with a downwardly-opening recess defined in part by an inner convex cylindrical surface, and at least one inwardly-directed protrusion below the recess with an upward-facing engagement surface, a downward-facing engagement surface, and a bottom surface below the downward-facing engagement surface,
wherein the inner concave cylindrical surface and the upper outer convex cylindrical surfaces of each upright arm of the receiver are configured to be closely received by the inner convex cylindrical surface and an opposing outer concave cylindrical surface of an arcuate recess of the tooling, respectively, when the at least one inwardly-directed protrusion of the receiver attachment portion of the tooling is positioned within the tool engagement groove and the downward-facing engagement surface of the inwardly-directed protrusion is closely received by the lower groove surface of the tool engagement groove, and
wherein after the elongate rod has been downwardly positioned into the open channel, the bottom surface the tooling does extend below a level of a top surface of the elongate rod.

16. The bone anchor system of claim 15, wherein the inwardly-facing inner cylindrical surface, the upper outer convex cylindrical surface, and the tool engagement groove are configured to provide for rotation of the receiver attachment portion of the tooling above the top surface of the elongate rod in both a clockwise direction and in a counter-clockwise direction.

17. The bone anchor system of claim 15, further comprising an upwardly-facing transition surface extending between the inner concave cylindrical surface and the discontinuous helically wound guide and advancement structure of the receiver, the inner concave cylindrical surface and upwardly-facing transition surface together defining an upwardly-facing inner tool engagement recess.

18. The bone anchor system of claim 17, wherein the upwardly-facing transition surface of the inner tool engagement recess is non-perpendicular to the inner concave cylindrical surface across a width thereof between the discontinuous helically wound guide and advancement structure and the inner concave cylindrical surface.

19. The bone anchor system of claim 17, wherein the upwardly-facing transition surface of the inner tool engagement recess slopes downwardly and radially outwardly away from the vertical centerline axis across a width thereof between the discontinuous helically wound guide and advancement structure and the inner concave cylindrical surface.

20. The bone anchor system of claim 15, wherein the tool engagement groove is curvate and extends circumferentially across an outermost of the upper outer convex cylindrical surfaces between the front face and the back face of the respective upright arm.

21. The bone anchor system of claim 15, further comprising a vertical slot formed into the upper outer convex cylindrical surface of each upright arm and extending downward from the top surface of the upright arm to at least the upper groove surface of the tool engagement groove.

22. The bone anchor system of claim 21, wherein the inner groove surface of the tool engagement groove is interrupted by the vertical slot.

23. The bone anchor system of claim 15, further comprising the shank and an inner open retaining ring configured to pivotably capture the head of the shank within the inner cavity of the receiver, with the shank extending downward through the lower opening, prior to securing the elongate rod in a locked configuration with the closure top.

* * * * *